United States Patent [19]
Cliff et al.

[11] Patent Number: 5,510,344
[45] Date of Patent: Apr. 23, 1996

[54] ACRYLATE FUNGICIDES

[75] Inventors: Geoffrey R. Cliff, Cambridge; Ian C. Richards, Suffolk, both of England

[73] Assignee: Schering Agrochemicals Limited, England

[21] Appl. No.: 237,689

[22] Filed: May 4, 1994

Related U.S. Application Data

[62] Division of Ser. No. 771,519, Oct. 4, 1991, Pat. No. 5,332,752, which is a continuation of Ser. No. 463,399, Jan. 11, 1990, abandoned.

[30] Foreign Application Priority Data

Jan. 11, 1989 [GB] United Kingdom .................. 8900578
Jan. 11, 1989 [GB] United Kingdom .................. 8900579
Jan. 11, 1989 [GB] United Kingdom .................. 8900581

[51] Int. Cl.$^6$ .................. C07D 227/14; A01N 43/78
[52] U.S. Cl. .................. 514/212; 514/239.2; 514/272; 514/312; 514/329; 514/352; 514/361; 514/367; 514/370; 514/372; 514/377; 514/380; 514/398; 514/426; 514/533; 514/538; 540/606; 544/164; 544/247; 546/171; 546/244; 546/335
[58] Field of Search .................. 548/194, 161, 548/128, 138, 214, 233, 245, 321.5, 558; 562/427, 432; 540/606; 544/164, 297; 546/171, 244, 335; 514/212, 234.2, 272, 312, 324, 352, 361, 367, 370, 372, 377, 386, 398, 426, 533, 538

[56] References Cited

FOREIGN PATENT DOCUMENTS 9117152 11/1991 WIPO .

*Primary Examiner*—Robert Gerstl
*Attorney, Agent, or Firm*—Ostrolenk, Faber, Gerb & Soffen

[57] ABSTRACT

Compounds of formula I

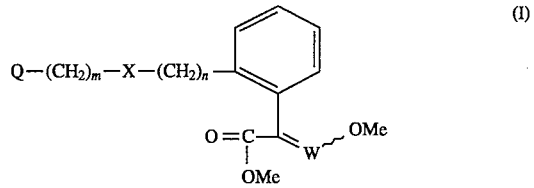

wherein X is oxygen or sulphur, W is CH or N, m is 0 or 1, and either a) n is 1 and Q is a non-aromatic heterocyclic ring of 3 to 10 ring atoms, containing one to three hetero atoms selected from oxygen, sulphur and nitrogen, which may be substituted and may be fused to another ring, with the proviso a) that if Q is thiazol-2-in-2-yl, it is substituted but not by methylene, and b) Q is not a six membered ring containing only two nitrogen atoms, or b) n is 0 or 1 and Q is

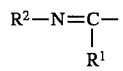

where $R^1$ is alkyl, alkoxy or alkylthio, and $R^2$ is heteroaryl, non aromatic heterocyclyl, optionally substituted cycloalkyl or optionally substituted alkyl containing at least 5 carbon atoms, phenyl substituted by one or more groups selected from halogen, optionally substituted alkyl, alkoxy, haloalkoxy, aryloxy, alkylthio and alkoxycarbonyl, and when $R^1$ is alkyl or alkoxy, or, when W is nitrogen, $R^2$ can also be unsubstituted phenyl, have pesticidal especially fungicidal activity.

15 Claims, No Drawings

ACRYLATE FUNGICIDES

This is a division of application Ser. No. 07/771,519, filed Oct. 4, 1991 U.S. Pat. No. 5,333,752 which is a continuation of Ser. No. 07/463,399 adandoned filed Jan. 11, 1990.

This invention relates to compounds having fungicidal activity.

Derivatives of acrylic acid having fungicidal activity have recently been described in a number of publications, and especially EP 178826 and 203608.

According to the invention there is provided a compound of formula I

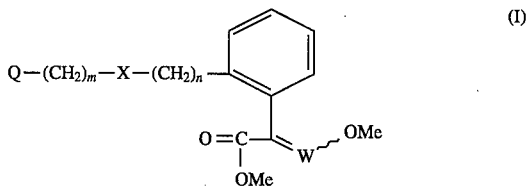

wherein

X is oxygen or sulphur,

W is CH or N, m is 0 or 1, and either a) n is 1 and Q is a non-aromatic heterocyclic ring of 3 to 10 ring atoms, containing one to three hetero atoms selected from oxygen, sulphur and nitrogen, which may be substituted and may be fused to another ring, with the proviso a) that if Q is thiazol-2-in-2-yl, it is substituted but not by methylene, and b) Q is not a six membered ring containing only two nitrogen atoms, or b) n is 0 or 1 and Q is

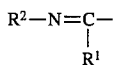

where $R^1$ is alkyl, alkoxy or alkylthio, and $R^2$ is heteroaryl, non aromatic heterocyclyl, optionally substituted cycloalkyl or optionally substituted alkyl containing at least 5 carbon atoms, phenyl substituted by one or more groups selected from halogen, optionally substituted alkyl, alkoxy, haloalkoxy, aryloxy, alkylthio and alkoxycarbonyl, and when $R^1$ is alkyl or alkoxy, or, when W is nitrogen, $R^2$ can also be unsubstituted phenyl, and acid addition salts of any compounds which are basic and basic addition salts of any compounds which are acidic.

When Q is a ring it is preferably a 5 to 7 membered ring. Examples include a) the group

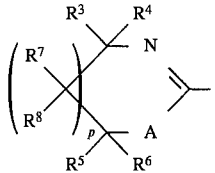

wherein

A is $CH_2$, S, O, NMe, NPh or CHMe, p is 0 or 1 and $R^3$, $R^4$, $R^5$, $R^6$, $R^7$ and $R^8$ are the same or different and are selected from hydrogen, alkyl, substituted alkyl (e.g. trifluoromethyl), alkenyl, substituted alkenyl, alkynyl, substituted alkynyl, alkoxy, haloalkoxy, alkylthio, haloalkylthio, halo, alkoxycarbonyl, oxoalkyl, aryl or optionally substituted amino, or i) $R^3$ and $R^4$, $R^5$ and $R^6$ or $R^7$ and $R^8$, together can form a further ring, which is either cycloalkyl or heterocyclyl, or ii) when p is 0 and A is $CH_2$ or CHMe, $R^3$ and $R^6$ together can form a bond or $R^4$ and $R^5$ together can form a fused ring, or iii) when p is 1, $R^3$ and $R^7$ or $R^6$ and $R^7$ together can form a bond or $R^4$ and $R^8$ or $R^5$ and $R^8$ together can form a fused ring, b) optionally substituted benzothiadiazinyl, or c) optionally substituted tetrahydroazepinyl.

Particularly preferred values of Q as a ring are substituted 1,3-thiazin-2-yl, substituted thiazol-2-in-2-yl and optionally substituted 3,1-benzothiazinyl.

When $R^2$ is alkyl, it is preferably of 5 to 15 carbon atoms and is optionally substituted, e.g. by halogen, alkoxy, alkylthio, alkoxycarbonyl or aryl. Otherwise alkyl, alkoxy or alkylthio groups are preferably of 1 to 4 carbon atoms, especially one carbon atom. Heteroaryl groups are aromatic rings which are preferably 5 or 6 membered and generally comprise 1 to 3 hetero atoms, e.g. oxygen, sulphur or nitrogen. These rings can be substituted and/or carry a fused ring especially a benzo ring. Examples of such groups include thienyl, furyl, pyrrolyl, pyridyl, pyrimidinyl, pyrazolyl, thiazolyl, oxazolyl, benzimidazolyl, tetrazolyl, benzoxazolyl, thiadiazolyl, triazolyl, imidazolyl or benzothiazolyl. Non-aromatic heterocyclyl are generally 5–8 membered rings which usually contain one to three hetero atoms such as oxygen, nitrogen or sulphur and can be substituted and/or carry fused rings. Examples of such groups include pyrrolidinyl, morpholinyl, thiomorpholinyl, or fully or partially hydrogenated thienyl, furanyl, pyrrolyl, thiazolyl, oxazolyl, oxazinyl, thiazinyl, pyridinyl and azepinyl. Cycloalkyl groups are generally of 3 to 8 carbon atoms. Aryl groups may be heteroaryl but are preferably phenyl, optionally substituted, e.g. by halogen, hydroxy, alkoxy, alkyl, trifluoromethyl or nitro.

$R^1$ is preferably methylthio or methyl.

A particularly preferred group of compounds are those where n is 1, m is 0 and X is S.

Compounds of the invention exist as structural isomers and the invention includes individual isomers as well as mixtures of these. Preferred compounds are those where the methoxypropenoate or (methoxyimino)acetate attached directly to the benzene ring shown in formula I is in the E-configuration.

The compounds of the invention are particularly valuable as fungicides, especially against fungal diseases of plants, e.g. mildews and particularly cereal powdery mildew (*Erysiphe graminis*), vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), potato blight (*Phytophthora infestans*), apple scab (*Venturia inaequalis*) and Septoria spp., e.g. *Septoria tritici* and *Septoria nodorum*. Other fungi against which the compounds may be active include other powdery mildews, other rusts, and general pathogens of Deuteromycete, Ascomycete, Phycomycete or Basidiomycete origin.

The compounds of the invention also have insecticidal, acaricidal and nematicidal activity and are particularly useful in combating a variety of economically important insects, acarids and plant nematodes, including animal ecto-parasites and especially Diptera, such as sheep blow-fly, *Lucilla sericata*, and house-flies, *Musca domestica*; Lepidoptera, including *Plutella xylostella, Spodoptera littoralis, Heliothis armigera* and *Pieris brassicae*; Homoptera, including aphids such as *Megoura viciae*; Coleoptera, including corn rootworms (Diabrotica spp., e.g. *Diabrotica undecimpunctata*); and spider mites, such as Tetranychus spp.

The invention thus also provides a method of combating pests (i.e. fungi, insects, nematodes and acarids) at a locus infested or liable to be infested therewith, which comprises applying to the locus a compound of formula I. The invention also provides an agricultural composition comprising a compound of formula I in admixture with an agriculturally acceptable diluent or carrier.

The composition of the invention may of course include more than one compound of the invention.

In addition the composition can comprise one or more additional active ingredients, for example compounds known to possess plant-growth regulant, herbicidal, fungicidal, insecticidal or acaricidal properties. Alternatively the compounds of the invention can be used in sequence with the other active ingredients.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, ethoxylated acetylenic glycols or ethoxylated tristyrylphenols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, (including coatings to form a seed pellet), a fumigant, a smoke, a bait, a dispersible powder, an emulsifiable concentrate or granules, e.g. water dispersible granulaes. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.0001 to 3.0 percent by weight, especially 0.001 to 0.1 percent by weight. In a primary composition the amount of active ingredient can vary widely and can be, for example, from 5 to 95 percent by weight of the composition.

In the method of the invention the compound is generally applied to seeds, plants or their habitat. Thus the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.005 to 10 kg per hectare, more preferably from 0.05 to 1 kg per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. However a later application to combat late diseases such as Septoria spp., may be advantageous. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.001 to 5 kg. per hectare, preferably from 0.005 to 1 kg per hectare.

The compounds of the invention may be prepared in a variety of ways, e.g. when n is 1, by reacting a compound of formula II

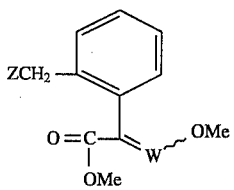

wherein Z is a leaving group, such as halogen, with a compound of formula III or a tautomer thereof

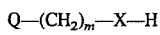

or, when Q is

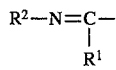

and m is 0, with a compound of formula IV

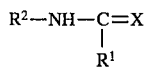

When Q is a non-aromatic heterocyclic ring as defined above a number of compounds of formula III are novel and these novel compounds form one aspect of the invention The invention is illustrated in the following Examples. Structures of isolated novel compounds were confirmed by elemental and/or other appropriate analyses. Temperatures are in °C.

EXAMPLE 1

Methyl o-tolylacetate (100 g) was dissolved in a mixture of methyl formate (450 ml) and dimethyl formamide (200 ml). The solution was added to a petrol washed suspension of sodium hydride (from 36.5 g of an 80% dispersion in oil) in dimethylformamide (100 ml) with cooling. The mixture was then stirred at room temperature overnight. Excess methyl formate and most of the dimethylformamide were evaporated and water (500 ml) was added. The mixture was treated with ether and the aqueous phase separated, acidified and extracted with ether. The extract was worked up in conventional manner to give a brown oil. This was dissolved in tetrahydrofuran and the solution added dropwise to sodium hydride (16.5 g of 80% dispersion in oil) in tetrahydrofuran (50 ml) with cooling. When hydrogen evolution had ceased, methyl iodide (35 ml) was added and the mixture heated to reflux for 5 hours. Methanol (5 ml) was added and the solvent evaporated. The resulting oil was partitioned between ether and water and the organic phase worked up in conventional manner to give to give methyl (Z)-3-methoxy-2-(o-tolyl)prop-2-enoate, m.p. 68°–70°. This product (185 g) was dissolved in carbon tetrachloride (1250 ml). N-Bromosuccinimide (159.3 g) was added and the mixture heated under reflux for 3 hours. The reaction mixture was then cooled and worked up to give a light brown oil. The crude product was triturated with a 10% solution of di-isopropyl ether in light petroleum to give methyl (E)-3-methoxy-2-[2-(bromomethyl)phenyl]prop-2-enoate, m.p. 87°–90° C., (Intermediate A).

Carbon disulphide (27 ml) was added to a mixture of (1S,2R)-(+)-norephedrine (5.0 g) and aqueous sodium hydroxide (50 ml of 15% solution) and the mixture stirred for 24 hours. Excess carbon disulphide was evaporated under reduced pressure and the residue poured into water and extracted with ethyl acetate. The extracts were washed with water, dried and evaporated. The residue was chromatographed on silica gel (eluent-ether/hexane; 1:1) to give 4-methyl-5-phenylthiazolidine-2-thione and 4-methyl-5-phenyloxazolidine-2-thione. A solution of the first of these thiones (0.80 g) in dimethylformamide was treated with sodium hydride (0.12 g of 80% dispersion in oil). When hydrogen evolution had ceased, intermediate A (1.2 g) was added, over one hour, and the mixture allowed to stand for 60 hours. The mixture was poured into water and extracted with ether. The extract was worked up in conventional manner to give methyl (E)-2-[2-[[(4-methyl-5-phenylthiazol-2-in-2 -yl)thio]methyl]phenyl]-3-methoxy-2-propenoate, as a gum. (Compound 1)

In a similar manner the other thione gave methyl (E)-2-[2-[[(4-methyl-5-phenyloxazol-2-in-2-yl)thio]-methyl]phenyl]-3-methoxy-2-propenoate, as a gum. (Compound 2)

EXAMPLE 2

Methyl chlorooxoacetate (22.5 ml) in tetrahydrofuran (60 ml) was added, dropwise, over one hour to a stirred solution of imidazole (33.35 g) in tetrahydrofuran (500 ml) maintained at 0°, under nitrogen. The mixture was then stirred for a further hour at this temperature. The reaction mixture was filtered and the precipitate washed with tetrahydrofuran. The filtrate and washings, containing methyl α-oxo-1 H-imidazole-1-acetate, were cooled to −65° C. and a solution of a Grignard reagent, prepared from o-bromotoluene (42 g), 1,2-dibromoethane (3.6 ml) and magnesium (7 g), in tetrahydrofuran, was added over 45 minutes, whilst maintaining the temperature between −60° and −70°. The mixture was then stirred at this temperature for 15 minutes and then at room temperature for 2½ hours. It was then poured into ice/water, extracted with ether, the extracts washed with brine, dried and concentrated. The residue was distilled under reduced pressure to give methyl oxo(o-tolyl)acetate, b.p. 92°–97°/0.5 mm. A solution of this a product (5 g) in methanol (100 ml) was heated under reflux for 3 hours with methoxyamine hydrochloride (2.55 g). The mixture was cooled, evaporated, triturated with diisopropyl ether, filtered and the filtrate evaporated to give methyl (methoxyimino)(o-tolyl)acetate. This was then treated with N-bromosuccinimide in carbon tetrachloride at reflux under a 300 watt lamp with the addition of benzoyl peroxide (0.005 g every 10 minutes). Conventional work up gave the bromomethyl compound (intermediate B) which was then reacted with substituted thiazolidinethione, derived from (1S,2R)-(+)-norephedrine, as described in Example 1, in a similar manner to that described in Example 1, to give methyl (methoxyimino){2-[[(4-methyl-5-phenylthiazol-2-in-2-yl)thio]methyl]phenyl}acetate, as a pale yellow gum. (Compound 3)

EXAMPLE 3

Methyl 4-methoxyphenyldithiocarbamate (4.5 g) was added to a suspension of sodium hydride (700 mg of 80% dispersion in oil), in tetrahydrofuran (50 ml). When hydrogen evolution had ceased, intermediate A from Example 1 (5.0 g) was added over one hour and the mixture allowed to stand for 36 hours. Aqueous sodium hydroxide was added and the mixture was extracted with diethyl ether and the extracts worked up in conventional manner to give methyl (E)-3-methoxy-2-[2-[[(4-methoxyphenylimino)(methylthio)methyl]thiomethylphenyl]-2-propenoate, as a pale yellow gum. (Compound 4).

EXAMPLE 4

Intermediate B from Example 2 was reacted with methyl 4-chlorophenyldithiocarbamate, in a similar manner to that described in Example 1, to give methyl [2-[[(4-chlorophenylimino)(methylthio)methyl]thiomethyl]phenyl] (methoxyimino)acetate, m.p. 74°–76° (Compound 5)

EXAMPLE 5

Methyl pyridin-3-yldithiocarbamate (1.85 ml) was added to a suspension of sodium hydride (350 mg of 80% dispersion in oil), in tetrahydrofuran (50 ml). When hydrogen evolution had ceased, intermediate A from Example 1 (2.5 g) was added over one hour and the mixture allowed to stand for 24 hours. The mixture was extracted with ethyl acetate and the extracts worked up in conventional manner to give methyl (E)-3-methoxy-2-[2-[[(pyridin-3-ylimino)(methylthio)methyl]thiomethyl]phenyl]-2-propenoate, as a yellow gum. (Compound 6)

EXAMPLE 6

Intermediate B from Example 2 was reacted with methyl benzothiazol-2-yldithiocarbamate, in a similar manner to that described in Example 1, to give methyl [2-[[(benzothiazol-2-ylimino)(methylthio)methyl]thiomethyl]phenyl] (methoxyimino)acetate, m.p. 106°–8° (Compound 7).

EXAMPLE 7

2-Aminopyrimidine (10.27 g) was dissolved in dimethyl sulphoxide (DMSO) (100 ml). A solution of sodium hydroxide (9.0 g) in water (20 ml) was added with stirring and cooling to less than 20°. After ten minutes, carbon disulphide (7.1 ml) was added dropwise over ten minutes, keeping the temperature between 10°–20° by cooling in ice. After stirring for a further 15 minutes, iodomethane (6.7 ml) was added dropwise at 10°–20° C. The reaction mixture was stirred for a further 20 minutes at room temperature and then poured into water (2000 ml). The solution was acidified with 2M hydrochloric acid. On standing for 30 minutes, a solid precipitated and was filtered. Trituration with ethyl acetate, gave methyl pyrimidin-2-yldithiocarbamate, m.p. 171°–3° C. (decomp) (sealed tube) in low yield.

This intermediate (0.5 g) was dissolved in dry DMSO (6 ml). A solution of intermediate A, from Example 1 (0.77 g) in dry DMSO (4 ml) was added. The mixture was warmed to 50° C. to give a clear solution which was then allowed to cool to room temperature and stirred for 3 hours. N,N-diisopropylethylamine (2 ml) was then added and the mixture stirred at room temperature for a further two hours before pouring on to water (200 ml). The mixture was extracted three times with ethyl acetate (80 ml). The extracts were combined, washed three times with 2M sodium hydroxide solution (80 ml) then dried over magnesium sulphate. Filtration and evaporation gave the crude product as a viscous brown oil that crystallised upon standing overnight. The product was dissolved in di-isopropyl ether containing a little ethyl acetate; decolourising charcoal (approximately 1 g) was added and the solution was filtered hot. Upon chilling the filtrate, a solid was precipitated. Filtration afforded methyl (E)-3-methoxy-2-{2-[(methylthio)(pyrimidin-2-ylimino)methylthiomethyl]phenyl}-2-propenoate, m.p. 109.5°–111° C. (Compound 8).

EXAMPLE 8

In a similar manner to that described in one of the previous Examples, the following compounds were obtained: Unless otherwise stated the compounds are in the E-form.

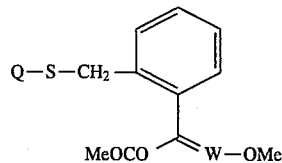

| Cpd no. | Q | W | m.p. (*) |
|---|---|---|---|
| 9 | 5-(4-MeO-phenyl)thiazol-2-in-2-yl | N | oil |
| 10 | 4-Me-5-Ph-thiazol-2-in-2-yl- | CH | gum |
| 11 | 4-Me-5-Ph-oxazol-2-in-2-yl- | CH | gum |
| 12 | 5-Ph-thiazol-2-in-2-yl- | CH | gum |
| 13 | 4,5-Ph$_2$-oxazol-2-in-2-yl- | CH | gum |
| 14 | 4-Et-thiazol-2-in-2-yl | CH | gum |
| 15 | 2-Me-1,1-dioxo-2H-1,2,4-benzothiadiazin-3-yl | CH | 125-7 |
| 16 | 4H-3,1-benzothiazin-2-yl | CH | gum |
| 17 | 4,5,6,7-tetrahydro-3H-azepin-2-yl | CH | gum |
| 18 | 4-Me-5-(3-hydroxyphenyl)thiazol-2-in-2-yl | CH | gum |
| 19 | 3,4,5,6-tetrahydropyridin-2-yl | CH | gum |
| 20 | 4-Ph-thiazol-2-in-2-yl | CH | gum |
| 21 | 4-Me-5-Ph-oxazol-2-in-2-yl | N | gum |
| 22 | 4H-3,1-benzothiazin-2-yl | N | gum |
| 23 | 5-phenylthiazol-2-in-2-yl | N | gum |
| 24 | (4-methylphenylimino)(MeS)methyl | CH | gum |
| 25 | (4-chlorophenylimino)(MeS)methyl | CH | gum |
| 26 | (3-trifluoromethylphenylimino)(MeS)methyl | CH | gum |
| 27 | (3-methoxyphenylimino)(MeS)methyl | CH | gum |
| 28 | (4-methoxycarbonylphenylimino)(MeS)methyl | CH | gum |
| 29 | (4-phenoxyphenylimino)(MeS)methyl | CH | gum |
| 30 | (4-t-butylphenylimino)(MeS)methyl | CH | gum |
| 31 | (4-propylphenylimino)(MeS)methyl | CH | 57–59 |
| 32 | (3-chlorophenylimino)(MeS)methyl | CH | oil |
| 33 | 1-(phenylimino)propyl | N | oil |
| 34 | (phenylimino)(MeS)methyl | N | oil |
| 35 | 4-Me-5-(3-hydroxyphenyl)oxazol-2-in-2-yl | CH | 67–69 |
| 36 | (4-Cl-benzothiazol-2-ylimino)(MeS)methyl | CH | 143-5 |
| 37 | (1,3-dimethylbutylimino)(MeS)methyl | CH | oil |
| 38 | (decylimino)(MeS)methyl | CH | oil |
| 39 | (dodecylimino)(MeS)methyl | CH | oil |
| 40 | (octylimino)(MeS)methyl | CH | oil |
| 41 | (hexahydroazepin-1-ylimino)(MeS)methyl | CH | oil |
| 42 | (pyridin-4-ylimino)(MeS)methyl | CH | oil |
| 43 | 4-ethoxycarbonylthiazol-2-in-2-yl | CH | Oil |
| 44 | 4-butyloxazol-2-in-2-yl | CH | oil |
| 45 | (morpholinoimino)(MeS)methyl | CH | oil |
| 46 | (2,2-dimethylpropylimino)(MeS)methyl | CH | oil |
| 47 | (5-chloropyridin-2-ylimino)(MeS)methyl | CH | oil |
| 48 | 5-phenyloxazol-2-in-2-yl | CH | oil |
| 49 | 4-butylthiazol-2-in-2-yl | CH | oil |
| 50 | 3a,4,5,6,7,7a-hexahydrobenzoxazol-2-yl | CH | oil |
| 51 | 5,5-dimethyl-4-ethoxycarbonyl-thiazol-2-in-2-yl | CH | oil |
| 52 | 5,5-dimethyl-4-butoxycarbonyl-thiazol-2-in-2-yl | CH | oil |
| 53 | (3,4-dichlorophenylimino)(MeS)methyl | CH | oil |
| 54 | 4-butoxycarbonylthiazol-2-in-2-yl | CH | 81-3 |
| 55 | 4-octyloxycarbonylthiazol-2-in-2-yl | CH | oil |
| 56 | 5,5-dimethyl-4-octyloxycarbonyl-thiazol-2-in-2-yl | CH | oil |
| 57 | 5-t-butyloxazol-2-in-2-yl | CH | oil |
| 58 | (1,2,3,4-tetrahydronaphth-1-yl-imino)(MeS)methyl | CH | oil |
| 59 | (2,4-difluorophenylimino)(MeS)methyl | CH | oil |
| 60 | 4-octylthiazol-2-in-2-yl | CH | oil |
| 61 | (4-butylphenylimino)(MeS)methyl | CH | oil |
| 62 | (2,5-difluorophenylimino)(MeS)methyl | CH | oil |
| 63 | pyrrol-1-in-2-yl | CH | 95-7 |

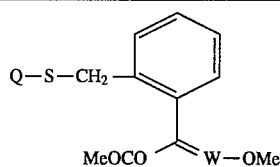

| Cpd no. | Q | W | m.p. (*) |
|---|---|---|---|
| 64 | 4,4,6-Me$_3$—4H-1,3-thiazin-2-yl | CH | 78–83 |
| 65 | 3-methylpyrrol-1-in-2-yl | CH | oil |
| 66 | [(N-methylanilino)imino](MeS)methyl | CH | oil |
| 67 | 4-(4-Cl-phenyl)pyrrol-1-in-2-yl | CH | oil |
| 68 | (3-methylisothiazol-5-ylimino)(MeS)methyl | CH | oil |
| 69 | (pyrimidin-2-ylimino)(MeS)methyl | CH | 109.5–11 |
| 70 | (5-methyl-1,3,4-thiadiazol-2-ylimino)(MeS)methyl | CH | 136–7 |
| 71 | 1-(4-chlorophenylimino)ethyl | CH | oil |
| 72 | 1-(pyridin-2-ylimino)ethyl | CH | oil |
| 73 | 1-(3-methylphenylimino)ethyl | CH | oil |
| 74 | 4,6,6-Me$_3$—6H-1,3-thiazin-2-yl | CH | 112–4 |
| 75 | cis-4,5-dimethyloxazol-2-in-2-yl | CH | oil |
| 76 | 5-(4-methoxyphenyl)thiazol-2-in-2-yl | CH | oil |
| 77 | (pyridin-2-ylimino)(MeS)methyl | CH | gum |
| 78 | (benzothiazol-2-ylimino)(MeS)methyl | CH | gum |
| 79 | (cyclohexylimino)(MeS)methyl | CH | 65 |
| 80 | (thiazol-2-ylimino)(MeS)methyl | CH | gum |
| 81 | (hexylimino)(MeS)methyl | CH | oil |
| 82 | (hexylimino)(MeS)methyl | N | oil |
| 83 | (piperidin-1-ylimino)(MeS)methyl | CH | 83–84 |
| 84 | (quinolin-8-ylimino)(MeS)methyl | CH | 101–2 |
| 85 | (6-MeO-benzothiazol-2-ylimino)(MeS)methyl | CH | 140–3 |
| 86 | (3-Me-imidazol-1-in-2-ylimino)(MeS)methyl | CH | 95–8 |
| 87 | (3-Me-isoxazol-5-ylimino)(MeS)methyl- | CH | 104–5 |
| 88 | (4,5,6,7-tetrahydrobenzothiazol-2-ylimino)(MeS)methyl | CH | 111–2 |
| 89 | (4,6-dimethylpyridin-2-ylimino)(MeS)methyl | CH | oil |
| 90 | (6-Me-benzothiazol-2-ylimino)(MeS)methyl- | CH | 141–2 |
| 91 | (2,6-dimethylpiperidinoimino)(MeS)methyl | CH | oil |
| 92 | 1,1-dioxo-2,3,4,5-tetrahydrothien-3-yl | CH | oil |
| 93 | 1-Ph-imidazol-2-in-1-yl.HCl | CH | 177–8 |
| 94 | [4-(4-chlorophenyl)thiazol-2-ylimino)-(MeS)methyl | CH | 116–8 |
| 95 | 1-(pyridin-2-ylimino)ethyl | CH | 100–2 |
| 96 | (2-methylphenylimino)(MeS)methyl | CH | oil |
| 97 | (2-methoxymethylpyrrolidinoimino)-(MeS)methyl | CH | oil |
| 98 | 4-butyloxazol-2-in-2-yl | N | oil |
| 99 | 5-methylpyrrol-1-in-2-yl | CH | oil |
| 100 | 1-Ph-imidazol-2-in-2-yl- | CH | gum |
| 101 | (6-MeO-pyridin-3-ylimino)(MeS)methyl | CH | oil |
| 102 | (4-Me-pyrimidin-2-ylimino)(MeS)methyl | CH | oil |
| 103 | (6-F-benzothiazol-2-ylimino)(MeS)methyl | CH | 125–7 |
| 104 | (3-phenyl-1,2,4-thiadiazol-5-ylimino)-(MeS)methyl | CH | 134–6 |
| 105 | 1-(3,4-dimethylphenylimino)ethyl | CH | 92–4 |
| 106 | (4,5,6,7-tetrahydro-3H-azepiri-2-ylimino)(MeS)methyl | N | oil |
| 107 | 4-butoxycarbonylthiazol-2-in-2-yl | N | 66–8 |
| 108 | (4-bromo-3-methylphenylimino)(MeS)methyl | CH | oil |
| 109 | (4-Me-benzothiazol-2-ylimino)(MeS)methyl | CH | 120–1 |
| 110 | 1-(4,6-dimethylpyrimidin-2-ylimino)ethyl | CH | 122–4 |
| 111 | (3-phenyl-1,2,4-thiadiazol-5-ylimino (MeS)methyl | N | 125–30 |
| 112 | (6-F-benzothiazol-2-ylimino)(MeS)methyl | N | 134–5 |
| 113 | 4,4-Me$_2$—4H-3,1-benzoxazin-2-yl | N | 95–7 |
| 114 | 5,6-dihydro-4,4,6-Me$_3$—4H-1,3-oxazin-2-yl | N | 95–7 |
| 115 | (morpholinoimino)(MeS)methyl (isomer 1) | N | 115–7 |
| 116 | (morpholinoimino)(MeS)methyl (isomer 2) | N | oil |

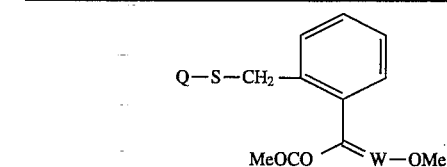

| Cpd no. | Q | W | m.p. (*) |
|---|---|---|---|
| 117 | 1,1-dioxo-2,3,4,5-tetrahydro-thien-3-yl (isomer 1) | N | 131–3 |
| 118 | 1,1-dioxo-2,3,4,5-tetrahydro-thien-3-yl (isomer 2) | N | oil |
| 119 | 5,6-dihydro-4,4,6-Me$_3$—4H-1,3-oxazin-2-yl | CH | 81–4 |
| 120 | 4,4-Me$_2$—4H-3,1-benzoxazin-2-yl | CH | oil |
| 121 | (5-CF$_3$-1,3,4-thiadiazol-2-ylimino)-(MeS)methyl | N | |
| 122 | 2,5-methylpyrrol-1-in-2-yl | N | oil |
| 123 | 5-hexylthiazol-2-in-2-yl | N | oil |
| 124 | (3-Me-isoxazol-5-ylimino)(MeS)methyl | N | 134–5 |
| 125 | (5-CF$_3$-1,3,4-thiadiazol-2-ylimino)-(MeS)methyl | CH | 79–80 |
| 126 | (quinolin-3-ylimino)(MeS)methyl | CH | 116–7 |
| 127 | (5-CF$_3$-pyridin-2-ylimino)(MeS)methyl | CH | 68–9 |
| 128 | (5-Br-pyridin-2-ylimino)(MeS)methyl | CH | 88–9 |
| 129 | (quinolin-2-ylimino)(MeS)methyl | N | 95–7 |
| 130 | trans-4,5-Me$_2$-oxazol-2-in-2-yl | CH | oil |
| 131 | 5-hexylthiazol-2-in-2-yl | CH | oil |
| 132 | 4-benzylthiazol-2-in-2-yl | CH | oil |
| 133 | 4-benzyloxazol-2-in-2-yl | CH | oil |
| 134 | 5-(3,4-dichlorophenyl)thiazol-2-in-2-yl | CH | oil |
| 135 | 5-(3,4-dichlorophenyl)oxazol-2-in-2-yl | CH | oil |
| 136 | 4-Et-5-Ph-oxazol-2-in-2-yl | CH | oil |
| 137 | 4-MeOCH$_2$-5-Ph-oxazol-2-in-2-yl | CH | oil |
| 138 | [5-(4-chlorophenyl)-1,3,4-oxadiazol-2-ylimino](MeS)methyl | CH | oil |

Notes:
Compounds 10, 11 and 21 were derived from (1R,2S)-(−)-norephedrine.

EXAMPLE 9

Allylamine and carbon disulphide were reacted together in the presence of triethylamine followed by reaction with intermediate A from Example 1 to give crude methyl 2-{2-[(allylaminothiocarbonyl)thiomethyl]phenyl}-3-methoxy-2-propenoate. This product (2.0 g), was dissolved in dichloromethane (10 ml) and triethylamine (0.85 ml) added. The mixture was cooled in an ice/salt bath to −6° C. and phenylsulphenyl chloride (0.87 g) was added. The temperature rose to 3° C. and the mixture was stirred in the ice/salt bath for 3 hours. Dichloromethane (15 ml) and 1M hydrochloric acid (20 ml) were added. The organic phase was separated and washed with aqueous sodium bicarbonate (20 ml) then dried over MgSO$_4$ and evaporated. Purification by column chromatography on silica gel using ethyl acetate/hexane (3:1) as eluant gave methyl 2-{2-[[(allylimino)(phenyldithio)methyl]thiomethyl]phenyl}-3-methoxy-2-propenoate. A solution of this product (0.1 g) in xylene (5 ml) was heated under reflux and irradiated by a uv lamp for 5 hours. Purification by preparative layer chromatography afforded methyl 3-methoxy-2-{2-[(5-phenyl-thiomethylthiazol-2-in-2-yl)thiomethyl]phenyl}-2-propenoate, as an oil, (compound 139)

Intermediate examples

Example A

This example illustrates an alternative method of preparing methyl oxo(o-tolyl)acetate, used as an intermediate in the preparation of compounds where W is N.

To a stirred solution of o-toluoyl chloride (38.86 g) in dichloromethane (250 ml) at room temperature was added water (20.0 ml) followed immediately by tetrabutylammonium bromide (0.15 g) and sodium cyanide (13.0 g). The reaction mixture was stirred vigorously for 1½ hours, then filtered. The filtrate was washed with water (2×100 ml) then dried (MgSO$_4$) and evaporated under reduced pressure to give a golden oil. Distillation under vacuum gave 2-methylbenzoyl cyanide, as a colourless oil, bp 47°–50°/0.05 mm. To 85% w/w sulphuric acid (140 ml) at room temperature was added sodium bromide (20 g) followed immediately by the dropwise addition of 2-methylbenzoyl cyanide (34.8 g). The reaction mixture was then heated gently until the exothermic reaction started and then maintained at 70° C. for 10 minutes by cooling. Methanol (400 ml) was added and the mixture heated under reflux for 1 hour, cooled and diluted with ice/water (500 ml). Extraction with diethyl ether gave a golden oil which was distilled under vacuum to give methyl oxo(o-tolyl)acetate, as B colourless oil, bp 75°–85°/0.4 mm.

Example B

This example illustrates the preparation of certain novel starting materials.

Method 1

To a stirred solution of 3-(N-phthalimido)butan-2-one (17 g) in 13% aqueous propan-2-ol (400 ml), sodium borohydride (14.7 g) was added portionwise. The temperature was maintained below 30° C. The clear solution was stirred at room temperature for 24 hours. Excess sodium borohydride was decomposed by dropwise addition of glacial acetic acid and the solvent was evaporated under reduced pressure. The residue was dissolved in water (500 ml) and the solution extracted with ethyl acetate (3×200 ml). The combined organic extracts were dried over sodium sulphate. Filtration and evaporation gave 2-hydroxymethyl-N-( 2-hydroxy-1-methylpropyl)-benzamide. This was dissolved in 20% aqueous ethanol (200 ml) containing sodium hydroxide (4 g) and the solution was heated under reflux for 5 hours and cooled. Hydrochloric acid (36%; 20 ml) was added and the solvent was evaporated under reduced pressure. The residue was suspended in water (200 ml) and extracted with ethyl acetate (3×200 ml). The combined organic extracts were discarded. The aqueous phase on evaporation under reduced pressure to approximately 80% volume, gave a solution of 3-aminobutan-2-ol hydrochloride. Sodium hydroxide pellets (30 g) were added portionwise with stirring and the cooled to 20° and stirred for 15 minutes. Carbon disulphide (100 ml) was added and the mixture was heated under reflux for 6 hours with vigorous stirring. The cooled reaction mixture was evaporated under reduced pressure to remove excess carbon disulphide. The residue was diluted to 300 ml with water, then extracted with diethyl ether (3×250 ml). The combined organic extracts were dried over sodium sulphate and evaporated to give a mixture of the geometrical isomers of 4,5-dimethyloxazolidine-2-thiones, as an oil. The aqueous phase was adjusted to pH 2 with hydrochloric acid (36%) and then extracted with ethyl acetate (3×100 ml). The combined organic extracts were dried over sodium sulphate. Filtration and evaporation gave an oil, which was dissolved in diethyl ether (100 ml) and filtered through a pad of silica-gel (20 mm×40 mm). The pad was washed with diethyl ether (100 ml) and the combined filtrates evaporated to give a second crop of 4,5-dimethyloxazolidine-2-thiones. The combined 4,5-dimethyloxazolidine-2-thiones were separated by flash chromatography on a silica-gel column using a 4:1 mixture of diethyl ether/light petroleum (bp: 40°–60°) as eluent, and the products were recrystallised from this solvent mixture to give trans-4,5-dimethyloxazolidine-2-thione, mp 82°–4°, and cis-4,5-dimethyloxazolidine-2-thione, mp 108°–9°.

Method 2

To a stirred cold solution of DL-2-amino-1-hexanol (1.1 ml) in dry THF (10 ml) was added triethylamine (2.8 ml) followed by dropwise addition of thiophosgene (0.81 ml) in dry THF (9 ml). The mixture was then stirred for 18 h at 20° C., evaporated under reduced pressure and the residue partitioned between water and diethylether. The ether extract was dried with sodium sulphate filtered and evaporated. The residue was dissolved in the minimum of hot 1:1 dimethylether-hexane and crystallised on cooling to give 4-butyloxazolidine-2-thione, mp 71°–2°.

In a similar manner to one of these two methods the following novel thiones were obtained:

| Thione for Cpd No | | mp (°) |
|---|---|---|
| 43 | 4-ethoxycarbonylthiazolidine-2-thione | oil |
| 52 | 5,5-dimethyl-4-butoxycarbonyl-thiazolidine-2-thione | 94–6 |
| 54 | 4-butoxycarbonylthiazolidine-2-thione- | oil |
| 55 | 4-octyloxycarbonylthiazolidine-2-thione | oil |
| 56 | 5,5-dimethyl-4-octyloxycarbonyl-thiazolidine-2-thione | oil |
| 57 | 5-t-butyloxazolidine-2-thione | 143–4 |
| 60 | 4-octylthiazolidine-2-thione | oil |
| 131 | 5-hexylthiazolidine-2-thione | 84–5 |
| 133 | 4-benzyloxazolidine-2-thione | oil |
| 134 | 5-(3,4-dichlorophenyl)thiazolidine-2-thione | oil |
| 135 | 5-(3,4-dichlorophenyl)oxazolidine-2-thione- | 113–5 |
| 136 | 4-Et-5-Ph-oxazolidine-2-thione | 124–5 |

NMR spectral data for compounds of the invention which do not have a characterising melting or boiling point Chemical shifts are measured in ppm in tetramethylsilane (TMS). Unless otherwise stated the solvent used was deuteriochloroform. The abbreviations have the following meanings:

| br | broad |
| d | doublet |
| m | multiplet |
| q | quartet |
| s | singlet |
| t | triplet |

| Cpd | NMR data (δ relative to TMS) |
|---|---|
| 1 | 1.35(3H, d, Me), 3.66(3H, s, OMe), 3.77(3H, s, OMe), 4.31(2H, s, CH$_2$), 4.4–4.7(2H, m, 2-CH), 7.0–7.55(9H, m, 9-ArH), 7.58(1H, s, CH). |
| 2 | 0.78(3H, d, Me), 3.66(3H, s, OMe), 3.8(3H, s, OMe), 4.24(2H, s, CH$_2$), 4.35–4.65(1H, m, CH), 5.66(1H, d, CH), 7.05–7.80(9H, m, 9–ArH), 7.81(1H, s, CH), |
| 3 | 1.33(3H, d, Me), 3.83(3H, s, OMe), 4.04(3H, s, OMe), 4.25(2H, s, CH$_2$), 4.30–4.70(4H, m, CH$_2$, 2-CH), 7.05–7.60(9H, m, 9–ArH). |
| 4 | 2.40(3H, s, SMe), 3.61(3H, s, OMe), 3.72(6H, d, 2-OMe), 4.22(2H, s, CH$_2$), 6.8(4H, s, 4-ArH), 7.0–7.45(4H, s, 4-ArH), 7.53(1H, s, CH). |
| 6 | 2.53(3H, s, SMe), 3.61(3H, s, OMe), 3.71(3H, s, OMe), 4.23(2H, s, CH$_2$), 7.1–7.5(6H, m, Ar), 7.56(1H, s, HC═C(Ar)CO$_2$Me), 8.20(1H, br, pyr-H), 8.31(1H, t, pyr-H). |
| 9 | 3.82(3H, s, OCH$_3$), 3.90(3H, s, CO$_2$CH$_3$), 4.09 (3H, s, NOCH$_3$), 4.24–4.38(1H, obscured m, Het-CH), 4.29 |

| Cpd | NMR data (δ relative to TMS) |
|---|---|
| | (2H, s, SCH$_2$), 4.48(1H, dd, Het-CH), 5.06(1H, dt, Het-CH), 6.8–6.9(2H, m, ArH), 7.1–7.45(5H, m, ArH), 7.55 (1H, m, ArH) |
| 10 | 1.37(3H, d, Me), 3.67(3.67, s, OMe), 3.80(3H, s, OMe), 4.32(2H, s, CH$_2$), 4.50–4.70(2H, m, 2-CH), 7.05–7.55(9H, m, 9-ArH), 7.60(1H, s, CH). |
| 11 | 0.77(3H, d, Me), 3.66(3H, s, OMe), 3.78(3H, s, OMe), 4.23(2H, s, CH$_2$), 4.35–4.6(1H, m, CH), 5.65(1H, d, CH), 7.0–7.45(9H, m, 9ArH), 7.48(1H, s, CH). |
| 12 | 3.66(3H, s, OMe), 3.76(3H, s, OMe), 4.25–4.6(4H, m, 2-CH$_2$), 5.04(1H, t, CH), 7.0–7.5(9H, m, 9-ArH), 7.56(1H, s, CH). |
| 13 | 3.66(3H, s, OMe), 3.76(3H, s, OMe), 4.35(2H, s, CH$_2$), 5.53(1H, d, CH), 5.87(1H, d, CH), 6.7–7.5(14H, m, 14-ArH), 7.6(1H, s, CH). |
| 14 | solvent: acetone-d$_6$ 1.10(3H, t, Me), 1.4–1.9(2H, m, CH$_2$), 3.1(1H, q, CH), 3.59(3H, s, OMe), 3.8(3H, s, OMe) 4.28(2H, s, CH$_2$), 6.95–7.55(4H, m, 4-ArH)7.6(1H, s, CH) |
| 16 | 3.67(3H, s, OMe), 3.76(3H, s, OMe), 3.83(3H, s, CH$_2$), 4.44(2H, s, CH$_2$), 6.9–7.4(8H, m, 8-ArH), 7.53(1H, s, CH). |
| 17 | 1.2–1.9(8H, m, 4-CH$_2$), 2.3–2.5(2H, m, CH$_2$), 3.67(3H, s, OMe), 3.81(3H, s, OMe), 4.07(2H, s, CH$_2$), 7.0–7.5(4H, m, 4-ArH), 7.55(1H, s, CH). |
| 18 | 1.5–1.85(6H, m, 3-CH$_2$), 2.1–2.35(2H, m, CH$_2$), 3.68(3H, s, OMe)3.81(3H, s, OMe)4.09(2H, s, CH$_2$), 7.0–7.5(4H, m, 4-ArH)7.53(1H, s, CH). |
| 19 | 1.71(2H, m, Het-CH$_2$), 2.26(1H, t, Het-CH$_2$), 3.7(3H, s, OCH$_3$), 3.7(2H, obscured t, Het-CH$_2$), 3.85 (3H, s, CO$_2$CH$_3$), 4.09(2H, s, SCH$_2$), 7.0–7.5(4H, m, ArH), 7.56(1H, s, =CH) |
| 20 | 3.5–3.85(8H, m, 2-OMe, CH$_2$), 4.35(2H, s, CH$_2$), 5.45(1H, t, CH), 7.0–7.45(9H, m, 9-ArH), 7.52(1H, s, CH). |
| 21 | 0.77(2H, d, Me), 3.82(3H, s, OMe), 4.04(3H, s, OMe), 4.18(2H, s, CH$_2$), 4.25–4.7(1H, m, CH), 5.65(1H, d, CH), 7.0–7.7(9H, m, 9-ArH). |
| 22 | 3.81(3H, s, OMe), 3.84(2H, s, CH$_2$), 4.05(3H, s, OMe), 4.39(2H, s, CH$_2$), 6.95–7.7(8H, m, 8-ArH) |
| 23 | 3.78(3H, s, OMe), 3.99(3H, s, OMe), 4.15–4.50(4H, m, 2-CH$_2$), 5.0(1H, t, CH), 7.05–7.60(9H, m, 8-ArH). |
| 24 | 2.28(3H, s, SMe), 2.41(3H, s, SMe), 3.63(3H, s, OMe), 3.73(3H, s, OMe), 4.24(2H, s, CH$_2$), 6.75–7.50(CH, m, 8-ArH), 7.57(1H, s, CH). |
| 25 | 2.41(3H, s, SMe), 3.62(3H, s, OMe), 3.72(3H, s, OMe), 4.21(2H, s, CH$_2$), 6.7–7.45(8H, m, 8-ArH), 7.54(1H, s, CH). |
| 26 | 2.41(3H, s, SMe), 3.61(3H, s, OMe), 3.70(3H, s, OMe), 4.23(2H, s, CH$_2$), 6.95–7.55(8H, m, 8-ArH), 7.57(1H, s, CH). |
| 27 | 2.42(3H, s, SMe), 3.53(3H, s, OMe), 3.63(3H, s, OMe), 3.66(3H, s, OMe), 4.22(2H, s, CH$_2$), 6.4–6.7(2H, m, ArH). |
| 28 | 2.42(3H, s, SMe), 3.63(3H, s, OMe), 3.71(3H, s, OMe), 4.24(2H, s, CH$_2$), 6.8–7.0(2H, d, 2-ArH), 7.0–7.55(4H, m, 4-ArH), 7.58(1H, s, CH) 7.9–8.1(2H, d, 2-ArH) |
| 29 | 2.42(3H, s, SMe), 3.63(3H, s, OMe), 3.73(3H, s, OMe), 4.25(2H, s, CH$_2$), 6.75–7.55(13H, m, 13-ArH), 7.59(1H, s, CH). |
| 30 | 1.27(9H, s, Bu$^t$), 2.41(3H, s, SMe), 3.62(3H, s, OMe), 3.70(3H, s, OMe), 4.24(2H, s, CH$_2$), 6.7–7.5(8H, m, ArH), 7.54(1H, s, CH). |
| 32 | 2.42(3H, s, SMe), 3.64(3H, s, OMe), 3.74(3H, s, OMe), 4.23(2H, s, CH$_2$), 6.65–7.45(8H, m, ArH), 7.56(1H, s, CH). |
| 33 | 1.03(3H, m, CH$_3$CH$_2$), 2.28(2H, m, CH$_3$CH$_2$), 3.74(3H, s, OMe), 4.01(3H, s, OMe), 4.12(2H, s, CH$_2$S), 6.71(2H, br d, ArH), 6.9–7.5(7H, br m, ArH). |
| 34 | (solvent:acetone-d$_6$) 2.41(3H, s, SMe), 3.70(3H, s, OMe), 3.94(3H, s, OMe), 4.23(2H, s, CH$_2$), 6.75–7.65(9H, m, ArH) |
| 37 | Mixture of E & Z imino isomers, 0.9(6H, m, CH(CH$_3$)$_2$), 1.0 & 1.1(3H, 2d, CH$_3$), 1.3(1H, m, CH), 1.5 (2H, m, CH$_2$), 2.35 & 2.5(3H, 2s, SCH$_3$), 3.7 (3H, m, OCH$_3$), 3.8(1H, m, NCH), 3.85(3H, s, CO$_2$CH$_3$), 4.15 & 4.25(2H, 2s, SCH$_2$), 7.1(1H, m, ArH), 7.25 (2H, m, ArH), 7.45(1H, m, ArH), 7.55 & 7.6(1H, 2s, =CH) |
| 38 | Mixture of E & Z imino isomers, 0.9(3H, t, CH$_3$), 1.2 (16H, br m, 8×CH$_2$), 2.35 & 2.45(3H, 2s, SCH$_3$), 3.4 (2H, m, NCH$_2$), 3.7(3H, s, OCH$_3$) 3.85(3H, s, CO$_2$CH$_3$), 4.15 & 4.25(2H, 2s, SCH$_2$), 7.1(1H, m, ArH), 7.25 (2H, m, ArH), 7.45(1H, m, ArH), 7.55 & 7.6(1H, 2s, =CH) |
| 39 | Mixture of E & Z imino isomers, 0.9(3H, t, CH$_3$), 1.2 (20H, br m, 10×CH$_2$), 2.35 & 2.45(3H, 2s, SCH$_3$), 3.4 (2H, m, NCH$_2$), 3.7(3H, d, OCH$_3$), 3.85(3H, d, CO$_2$CH$_3$), 4.2(2H, d, SCH$_2$), 7.1(1H, m, ArH), 7.25(2H, m, ArH), 7.45 (1H, m, ArH), 7.6(1H, d, =CH) |
| 40 | Mixture of E & Z imino isomers, 0.9(3H, m, CH$_3$), 1.2 (12H, br s, 6×CH$_2$), 2.35 & 2.45(3H, 2s, SCH$_3$), 3.4 (2H, m, NCH$_2$), 3.7(3H, s, OCH$_3$), 3.85(3H, s, CO$_2$CH$_3$), 4.15 & 4.25(2H, 2s, SCH$_2$), 7.1(1H, m, ArH), 7.25 (2H, m, ArH), 7.45(1H, m, ArH), 7.6(4H, d, =CH) |
| 41 | Mixture of E & Z imino isomers, 1.65(8H, br m, 4×CH$_2$), 2.35 & 2.45(3H, 2s, SCH$_3$), 2.95(4H, m, 2×NCH$_2$), 3.7 (3H, s, OCH$_3$), 3.85(3H, s, CO$_2$CH$_3$), 4.1 & 4.25 (2H, 2s, SCH$_2$), 7.15(1H, m, ArH), 7.3(2H, m, ArH), 7.5 (1H, m, ArH), 7.6(1H, d, =CH) |
| 42 | 2.5(3H, s, SCH$_3$), 3.75(3H, s, OCH$_3$), 3.8(3H, s, CO$_2$CH$_3$), 4.25(2H, br s, SCH$_2$), 6.8(2H, m, ArH), 7.15(1H, m, ArH), 7.3(2H, m, ArH), 7.45(1H, m, ArH), 7.6(1H, s, =CH), 8.5(2H, m, ArH) |
| 43 | 1.35(3H, t, CH$_3$), 3.65(2H, m, Het-CH$_2$), 3.7 (3H, s, OCH$_3$), 3.82(3H, s, CO$_2$CH$_3$), 4.28(2H, q, OCH$_2$CH$_3$), 4.35(2H, s, SCH$_2$Ar), 5.02(1H, t, Het-CH), 7.1–7.5(4H, m, ArH), 7.6(1H, s, =CH) |
| 44 | 0.95(3H, t, CH$_3$), 1.38–1.7(6H, m, 3×CH$_2$), 3.7 (3H, s, OCH$_3$), 3.8(3H, s, CO$_2$CH$_3$), 3.95(1H, dd, Het-CH), 4.14(1H, m, Het-CH), 4.2(2H, s, SCH$_2$Ar), 4.4 (1H, dd, Het-CH), 7.15(4H, m, ArH), 7.6(1H, s, =CH) |
| 45 | Mixture of E & Z imino isomers, 2.35 & 2.45 (3H, 2s, SCH$_3$), 2.8(4H, m, 2×NCH$_2$), 3.7(3H, d, OCH$_3$), 3.8(4H, m, 2×OCH$_2$), 3.9(3H, d, CO$_2$CH$_3$), 4.1 & 4.2 (2H, 2s, SCH$_2$), 7.15(1H, m, ArH), 7.3(2H, m, ArH), 7.5 (1H, m, ArH), 7.6(1H, d, =CH) |
| 46 | Mixture of E & Z imino isomers, 0.95 & 1.0 (9H, 2s, C(CH$_3$)$_3$), 2.4 & 2.5(3H, 2s, SCH$_3$), 3.05 & 3.1(2H, 2s, NCH$_2$), 3.7(3H, s, OCH$_3$), 3.8(3H, d, CO$_2$CH$_3$), 4.25(2H, br s, SCH$_2$), 7.15(1H, m, ArH), 7.3 (2H, m, ArH), 7.5(1H, m, ArH), 7.6(1H, d, =CH) |
| 47 | 2.5(3H, s, SCH$_3$), 3.7(3H, s, OCH$_3$), 3.8(3H, s, CO$_2$CH$_3$), 4.3(2H, br s, SCH$_2$), 6.95(1H, d, ArH), 7.15(1H, m, ArH), 7.25(2H, m, ArH), 7.35(1H, m, ArH), 7.6(2H, m, ArH), 8.4(1H, s, =CH) |
| 48 | 3.73(3H, s, OCH$_3$), 3.77–3.93(4H, m, Het-CH & CO$_2$CH$_3$), 4.2–4.42(3H, m, Het-CH & SCH$_2$), 5.6(1H, t, OCH), 7.1–7.6(9H, m, ArH), 7.62(1H, s, =CH) |
| 49 | 0.95(3H, t, CH$_3$), 1.4–1.8(6H, m, 3×CH$_2$), 3.06 (1H, dd, Het-CH), 3.5(1H, m, Het-CH), 3.75(3H, s, OCH$_3$), 3.82(3H, s, CO$_2$CH$_3$), 4.3(2H, s, SCH$_2$Ar), 4.4 (1H, m, Het-CH), 7.1–7.5(4H, m, ArH), 7.6(1H, s, =CH) |
| 50 | 1.35–2.35(8H, m, 4×CH$_2$), 3.24(1H, dt, Het-CH), 3.7 (1H, m, Het-CH), 3.7(3H, s, OCH$_3$), 3.8(3H, s, CO$_2$CH$_3$), 4.22(2H, q, SCH$_2$Ar), 7.1–7.5(4H, m, ArH), 7.6 (1H, s, =CH). |
| 51 | 1.35(3H, t, CO$_2$CH$_3$), 1.42(3H, s, CH$_3$), 1.75 (3H, s, CH$_3$), 3.7(3H, s, OCH$_3$), 3.84(3H, s, CO$_2$CH$_3$), 4.28 (2H, q, CO$_2$CH$_2$CH$_3$), 4.34(2H, s, SCH$_2$Ar), 4.65(1H, s, Het-CH), 7.15–7.54(4H, m, ArH), 7.6(1H, s, =CH) |
| 52 | 0.95(3H, t, CO$_2$(CH$_2$)$_3$CH$_3$), 1.4(3H, s, CH$_3$), 1.44 (2H, m, CO$_2$(CH$_2$)$_2$CH$_2$CH$_3$), 1.68(2H, m, CO$_2$(CH$_2$)$_2$CH$_2$CH$_2$CH$_3$), 1.7(3H, s, CH$_3$), 3.68(3H, s, OCH$_3$), 3.84(3H, s, CO$_2$CH$_3$), 4.2(2H, m, CO$_2$CH$_2$(CH$_2$)$_2$CH$_3$), 4.34(2H, s, SCH$_2$Ar),4.66(1H, s, Het-CH), 7.12–7.5(4H, m, ArH), 7.6(1H, s, =CH). |
| 53 | 2.5(3H, s, SCH$_3$), 3.7(3H, s, OCH$_3$), 3.8(3H, s, CO$_2$CH$_3$), 4.25(2H, br s, SCH$_2$), 6.7(1H, m, ArH), 7.0(1H, m, ArH), 7.1(1H, m, ArH), 7.3(3H, m, ArH), 7.5(1H, m, ArH), 7.6 (1H, s, =CH) |
| 55 | 0.95(3H, t, (CH$_2$)$_7$CH$_3$), 1.35(10H, m, CH$_2$CH$_2$(CH$_2$)$_5$CH$_3$), 1.72(2H, m, CH$_2$CH$_2$(CH$_2$)$_5$CH$_3$), 3.64(2H, m, Het-CH$_2$), 3.7 (3H, s, OCH$_3$), 3.84(3H, s, CO$_2$CH$_3$), 4.22 (2H, t, CH$_2$(CH$_2$)$_6$CH$_3$), 4.35(2H, s, SCH$_2$Ar), 5.06 (1H, t, Het-CH), 7.01–7.5(4H, m, ArH), 7.6(1H, s, =CH) |
| 56 | 0.95(3H, t, (CH$_2$)$_7$CH$_3$), 1.3(10H, m, CH$_2$CH$_2$(CH$_2$)$_5$CH$_3$), 1.44(3H, s, CH$_3$), 1.68(2H, m, CH$_2$CH$_2$(CH$_2$)$_5$CH$_3$), 1.74(3H, s, CH$_3$), 3.7(3H, s, OCH$_3$), 3.84(3H, s, CO$_2$CH$_3$), 4.22(2H, t, CH$_2$(CH$_2$)$_6$CH$_3$), 4.35(2H, s, SCH$_2$Ar), 4.68 (1H, s, Het-CH), 7.12–7.51(4H, m, ArH), 7.6(1H, s, =CH) |
| 57 | 0.95(9H, s, 3×CH$_3$), 3.64(1H, m, Het-CH), 3.7 (3H, s, OCH$_3$), 3.8(1H, m, Het-CH), 3.84(4H, s, CO$_2$CH$_3$), |

| Cpd | NMR data (δ relative to TMS) |
|---|---|
|  | 4.18(2H, s, SCH$_2$Ar), 4.36(1H, m, Het-CH), 7.1–7.5 (4H, m, ArH), 7.6(1H, s, =CH) |
| 58 | Mixture of E & Z imino isomers, 1.6–2.1(4H, m, 2×CH$_2$), 2.4 & 2.5(3H, 2s, SCH$_3$), 2.9(2H, m, ArCH$_2$), 3.7 (3H, s, OCH$_3$), 3.75 & 3.85(3H, 2s, CO$_2$CH$_3$), 4.2 & 4.3 (2H, 2s, SCH$_2$), 5.0(1H, m, ArCHN), 7.0–7.4(8H, m, ArH), 7.55 & 7.65(1H, 2s, =CH) |
| 59 | 2.5(3H, br s, SCH$_3$), 3.7(3H, s, OCH$_3$), 3.8 (3H, s, CO$_2$CH$_3$), 4.3(2H, br s, SCH$_2$), 6.8–7.5 (7H, m, ArH), 7.6(1H, s, =CH) |
| 60 | 0.95(3H, t, (CH$_2$)$_7$CH$_3$), 1.3–1.8(14H, m,(CH$_2$)$_7$CH$_3$), 3.04(1H, m, Het-CH), 3.44(1H, m, Het-CH), 3.7 (3H, s, OCH$_3$), 3.84(3H, s, CO$_2$CH$_3$), 4.28(2H, s, SCH$_2$Ar), 4.37(1H, m, Het-CH), 7.1–7.5(4H, m, ArH), 7.6 (1H, s, =CH) |
| 61 | 0.9(3H, t, CH$_3$), 1.3(2H, m, CH$_2$), 1.6(2H, m, CH$_2$), 2.4 (3H, br s, SCH$_3$), 2.5(2H, t, NCH$_2$), 3.7(3H, s, OCH$_3$), 3.8(3H, s, CO$_2$CH$_3$), 4.25(2H, br s, SCH$_2$), 6.8 (2H, d, ArH), 7.1(3H, m, ArH), 7.3(2H, d, ArH), 7.45 (1H, br s, ArH), 7.5(1H, s, =CH), |
| 62 | 2.5(3H, s, SCH$_3$), 3.7(3H, s, OCH$_3$), 3.8(3H, s, CO$_2$CH$_3$), 4.3(2H, s, SCH$_2$), 6.65(1H, m, ArH), 6.75(1H, m, ArH), 7.0(1H, m, ArH), 7.1(1H, m, ArH), 7.3(2H, m, ArH), 7.45(1H, m, ArH), 7.6(1H, s, =CH) |
| 65 | 1.15(3H, d, CH$_3$), 1.62, 2.27 & 2.86,(1H, each, m, Het-CH), 3.71(3H, s, OCH$_3$), 3.76(1H, m, Het-CH), 3.92 (1H, m, Het-CH), 3.84(3H, s, CO$_2$CH$_3$), 4.21(2H, s, SCH$_2$), 7.0–7.5(4H, m, ArH), 7.55(1H, s, =CH) |
| 66 | Mixture of E & Z imino isomers, 2.35 & 2.6 (3H, 2s, SCH$_3$), 3.05 & 3.1(3H, 2s, NCH$_3$), 3.65 & 3.7 (3H, 2s, OCH$_3$), 3.7 & 3.8(3H, 2s, CO$_2$CH$_3$), 4.1 & 4.4 (2H, 2s, SCH$_2$), 6.9–7.5(9H, m, ArH), 7.55 & 7.65 (1H, 2s, =CH) |
| 67 | 2.68, 3.05 & 3.59(1H each, m, Het-CH), 3.71 (3H, s, OCH$_3$), 3.85(3H, s, CO$_2$CH$_3$), 3.88(1H, m, Het-CH), 4.3(1H, s, SCH$_2$), 4.38(1H, m, Het-CH), 7.0–7.55 (4H, m, ArH), 7.61(1H, s, =CH) |
| 68 | 2.43(3H, s, CH$_3$), 2.57(3H, s, SCH$_3$), 3.70(3H, s, OCH$_3$), 3.84(3H, s, CO$_2$CH$_3$), 4.36(2H, s, CH$_2$), 6.72(1H, s, Het-CH), 7.10–7.48(4H, m, ArH), 7.60(1H, s, =CH) |
| 71 | 1.98(3H, s, N=CCH$_3$), 3.73(3H, s, OCH$_3$), 3.82 (3H, s, CO$_2$CH$_3$), 4.25(2H, br s, SCH$_2$), 6.75(2H, d, ArH), 7.15(1H, t, ArH), 7.30(4H, m, ArH), 7.46(1H, t, ArH), 7.59(1H, s, =CH) |
| 72 | 2.12(3H, br s, N=C—CH$_3$), 3.70(3H, s, OCH$_3$), 3.80 (3H, s, CO$_2$CH$_3$), 4.25(2H, br s, SCH$_2$), 6.82(1H, d, ArH) , 7.00(1H, m, ArH), 7.15(1H, m, ArH), 7.28(2H, m, ArH), 7.52(1H, M, ArH), 7.60(1H, s, =CH), 7.68(1H, t, ArH), 8.40(1H, d, ArH) |
| 73 | 2.0(3H, s, N=CCH$_3$), 2.36(3H, s, ArCH$_3$), 3.70 (3H, s, OCH$_3$), 3.82(3H, s, CO$_2$CH$_3$), 4.25(2H, br s, SCH$_2$), 6.60(2H, d, ArH), 6.90(1H, d, ArH), 7.1–7.35 (4H, m, ArH), 7.52(1H, m, ArH), 7.6(1H, s, =CH) |
| 75 | 1.18(3H, d, CH$_3$), 1.3(3H, d, CH$_3$), 3.72(3H, s, OCH$_3$), 3.85(3H, s, CO$_2$CH$_3$), 4.1(1H, m, Het-CH), 4.15 (2H, s, SCH$_2$Ar) , 4.78(1H, m, Het-CH), 7.12–7.5 (4H, m, ArH), 7.6(1H, s, =CH) |
| 76 | 3.7(3H, s, OCH$_3$), 3.8(3H, s, ArOCH$_3$), 3.84 (3H, s, CO$_2$CH$_3$), 4.3(1H, m, Het-CH), 4.35(2H, s, SCH$_2$Ar), 4.5(1H, m, Het-CH), 5.06(1H, m, Het-CH), 6.85–7.5(8H, m, ArH), 7.6(1H, s, =CH). |
| 77 | 2.47(3H, s, SMe), 3.63(3H, s, OMe), 3.76(3H, s, OMe), 4.29(2H, s, CH$_2$), 6.9–7.7(7H, br m, Ar), 7.57(1H, s, HC=C(Ar)CO$_2$Me), 8.40(1H, br d, pyr-H). |
| 78 | 2.53(3H, s, SMe), 3.65(3H, s, OMe), 3.78(3H, s, OMe), 4.35(2H, s, CH$_2$), 7.05–7.55(6H, br m, ArH), 7.58(1H, s, HC=C(Ar)CO$_2$Me), 7.7–7.8(2H, br m, ArH). |
| 80 | 2.52(3H, s, SMe), 3.67(3H, s, OMe), 3.80(3H, s, OMe), 4.34(2H, s, C$_2$), 6.5–7.5(6H, br m, ArH), 7.49(1H, s, HC=C(Ar)CO$_2$Me). |
| 81 | mixture of isomers: 0.87(3H, br t, CH$_3$CH$_2$—), 1.1–1.5(6H, br m,(CH$_2$)$_3$), 1.5–1.8(2H, br m, CH$_2$), 2.33 and 2.43(3H, 2×s, SMe), 3.39(2H, br t, CH$_2$N), 3.66(3H, s, OMe), 3.78(3H, s, OMe), 4.17 and 4.20(2H, 2×br s, SCH$_2$Ar), 7.0–7.5(4H, m, Ph), 7.53 and 7.58(1H, 2×s, HC=C(Ar)CO$_2$Me). |
| 82 | mixture of isomers: 0.86(3H, br t, CH$_3$CH$_2$—), 1.1–1.45(6H, br m,(CH$_2$)$_3$), 1.45–1.8(2H, br m, CH$_2$), 2.32 |
|  | and 2.43(3H, 2×s, SMe), 3.38(2H, t, CH$_2$N), 3.82(3H, s, OMe), 4.01(3H, s, OMe), 4.11 and 4.15(2H, 2×br s, SCH$_2$Ar), 6.9–7.6(4H, br m, Ph). |
| 89 | 2.32(3H, s, CH$_3$), 2.51(6H, s, 2×CH$_3$), 3.71 (3H, s, OCH$_3$), 3.81(3H, s, CO$_2$CH$_3$), 6.57(1H, d, pyridine ring CH), 6.72(1H, d, pyridine ring CH), 7.08–7.53 (4H, m, ArH), 7.60(1H, s, =CH) |
| 91 | 0.9(6H, d, 2×CH$_3$), 1.4–1.7(6H, m, 3×CH$_2$), 2.3 (3H, s, SCH$_3$), 2.5(2H, br s, N—CH), 3.7(3H, s, OCH$_3$), 3.85(3H, s, CO$_2$CH$_3$), 4.25(2H, s, SCH$_2$), 7.1(1H, m, ArH), 7.3(2H, m, ArH), 7.55(1H, m, ArH), 7.6(1H, s, =CH) |
| 92 | 2.36, 2.79 & 2.97(1H each, m, Het-CH), 3.1–3.4 (3H, m, 3×Het-CH), 3.70(2H, s, CH$_2$), 3.75(3H, s, OCH$_3$), 3.7–3.8(1H, obscured m, Het-CH), 3.88(3H, s, CO$_2$CH$_3$), 7.14(1H, m, ArH), 7.30(2H, m, ArH), 7.44(1H, m, ArH), 7.61(1H, s, =CH) |
| 96 | 2.1(3H, s, ArCH$_3$), 2.5(3H, s, SCH$_3$), 3.65(3H, s, OCH$_3$), 3.8(3H, s, CO$_2$CH$_3$), 4.3(2H, br s, SCH$_2$), 6.8 (1H, m, ArH), 7.0(1H, m, ArH), 7.1(3H, m, ArH), 7.3 (2H, m, ArH), 7.5(1H, m, ArH), 7.6(1H, s, =CH) |
| 97 | Mixture of E & Z imino isomers, 1.65–2.05 (4H, m, 2×CH$_2$), 2.2 & 2.25(3H, 2s, SCH$_3$), 2.5 (1H, m, NCH), 3.2–3.45(4H, m, NCH$_2$ & OCH$_2$), 3.4 (3H, d, OCH$_3$), 3.7(3H, s, OCH$_3$), 3.85(3H, s, CO$_2$CH$_3$), 7.1(1H, m, ArH), 7.25(2H, m, ArH), 7.5(1H, m, ArH), 7.6 (1H, d, =CH) |
| 98 | 0.94(3H, t, CH$_3$), 1.15–1.8(6H, m, 3×CH$_2$), 3.86 (3H, s, CO$_2$CH$_3$), 3.93(1H, t, Het-CH), 4.0–4.2 (1H, obscured m, Het-CH), 4.08(3H, s, NOCH$_3$), 4.15 (2H, s, CH$_2$S), 4.41(1H, t, Het-CH), 7.14(1H, dd, ArH), 7.3–7.45(2H, m, ArH), 7.58(1H, dd, ArH) |
| 99 | 1.30(3H, d, CH$_3$), 1.53, 2.20(1H each, m, Het-CH), 2.62 (2H, m, Het-CH), 3.71(3H, s, OCH$_3$), 3.85(3H, s, CO$_2$CH$_3$), 4.11(1H, m, Het-CH), 4.26(2H, q, CH$_2$S), 7.0–7.5 (4H, m, ArH), 7.59(1H, s, =CH) |
| 100 | 3.62(3H, s, OCH$_3$), 3.76(3H, s, CO$_2$Me), 3.95(4H, t, Het-CH), 4.29(2H, s, CH$_2$S), 7.0–7.5(9H, m, ArH), 7.56 (1H, s, =CH) |
| 101 | 2.50(3H, s, SCH$_3$), 3.68(3H, s, OCH$_3$), 3.80 (3H, s, CO$_2$CH$_3$), 3.90(3H, s, ArOCH$_3$), 4.29(2H, s, SCH$_2$), 6.70(1H, d, pyridine H), 7.05–7.5(5H, m, 4×ArH & pyridine H), 7.60(1H, s, =CH), 7.77(1H, s, pyridine H) |
| 102 | 2.54(6H, s, SCH$_3$ & CH$_3$), 3.70(3H, s, OCH$_3$), 3.82 (3H, s, CO$_2$CH$_3$), 4.26(2H, s, SCH$_2$), 6.84 (1H, d, pyrimidine H), 7.0–7.5(4H, m, ArH), 7.60(1H, s, =CH), 8.52(1H, d, pyrimidine H) |
| 106 | 1.45–1.65(4H, m, 2×Het-CH$_2$), 1.74–1.86(2H, m, Het-CH$_2$), 2.35–2.45(2H, m, Het-CH$_2$), 3.67(2H, m, Het-CH$_2$N), 3.87 (3H, s, CO$_2$CH$_3$), 4.03(2H, s, SCH$_2$), 4.09(3H, s, NOCH$_3$), 7.11(1H, m, ArH), 7.2–7.4(2H, m, ArH), 7.46 (1H, m, ArH) |
| 108 | 2.37(3H, s, ArCH$_3$), 2.47(3H, s, SCH$_3$), 3.7 (3H, s, OCH$_3$), 3.8(3H, s, CO$_2$CH$_3$), 4.26(2H, br s, SCH$_2$), 6.6(1H, d, ArH), 6.8(1H, s, ArH), 7.14(1H, br d, ArH), 7.23–7.35(2H, m, ArH), 7.4–7.55(2H, m, ArH), 7.58 (1H, s, =CH) |
| 116 | 2.45(3H, s, CH$_3$S), 2.7–2.85(4H, m, Het-CH), 3.68–3.84 (4H, m, Het-CH), 3.86(3H, s, CO$_2$CH$_3$), 4.06(5H, br s, SCH$_2$ & NOCH$_3$), 7.1–7.18(1H, m, ArH), 7.25–7.55 (3H, m, ArH) |
| 118 | 2.0(1H, m, Het-CH), 2.2(1H, br m, Het-CH), 2.77 (1H, q, Het-CH), 2.85–3.3(4H, m, Het-CH), 3.8 (2H, s, SCH$_2$), 3.94(3H, s, CO$_2$CH$_3$), 4.08(3H, s, NOCH$_3$), 7.17(1H, m, ArH), 7.3–7.5(3H, m, ArH) |
| 120 | 1.63(6H, s, 2×CH$_3$), 3.72(3H, s, OCH$_3$), 3.88 (3H, s, CO$_2$CH$_3$), 4.30(2H, s, CH$_2$S), 7.05–7.35 (7H, m, ArH), 7.60(1H, m, ArH), 7.64(1H, s, =CH) |
| 122 | Obtained as a mixture of diastereisomers - separated by column chromatograchy NMR for major diasteroisomers: 1.3(3H, d, CH$_3$), 1.52(1H, m, Het-CH), 2.22(1H, m, Het-CH), 2.6(2H, m, 2×Het-CH), 3.86 (3H, s, CO$_2$CH$_3$), 4.06(3H, s, NOCH$_3$), 4.0–4.2 (1H, obscured m, Het-CH), 4.22(2H, s, SCH$_2$), 7.14 (1H, m, ArH), 7.24–7.32(2H, m, ArH), 7.54(1H, m, ArH) |
| 123 | 0.9(3H, br t, CH$_3$), 1.18–1.45(8H, m, 4×CH$_2$), 1.70 (2H, m, CH$_2$), 3.82–4.36(5H, obscured m, CH$_2$S & 3×Het-CH), 3.88(3H, obscured s, CO$_2$CH$_3$), 4.06(3H, |

-continued

| Cpd | NMR data (δ relative to TMS) |
|---|---|
| | obscured s, NOCH$_3$), 7.14(1H, m, ArH), 7.23–7.46(2H, m, ArH), 7.53(1H, m, ArH) |
| 130 | 1.3(3H, d, CH$_3$), 1.38(3H, d, CH$_3$), 3.7(3H, s, OCH$_3$), 3.74(1H, m, Het-CH), 3.84(3H, s, CO$_2$CH$_3$), 4.2 (2H, s, SCH$_2$Ar), 4.25(1H, m, Het-CH), 7.15–7.52 (4H, m, ArH), 7.6(1H, s, =CH) |
| 131 | 0.95(3H, t,(CH$_2$)$_5$CH$_3$), 1.3(8H, s, CH$_2$(CH$_2$)$_4$CH$_3$), 1.64(2H, m, CH$_2$(CH$_2$)$_4$CH$_3$), 3.7(3H, s, OCH$_3$), 3.85 (3H, s, CO$_2$CH$_3$), 3.95(2H, m, Het-CH), 4.2(1H, m, Het-CH), 4.3(2H, s, SCH$_2$Ar), 7.14–7.45(4H, m, ArH), 7.6 (1H, s, =CH) |
| 132 | 2.62 & 3.16(2H, 2dd, non equivalent ARCH$_2$), 3.35 (1H, m, Het-CH), 3.7(3H, s, OCH$_3$), 3.84(3H, s, CO$_2$CH$_3$), 4.35(2H, s, SCH$_2$Ar), 4.72(1H, m, Het-CH), 7.14–7.48 (9H, m, ArH), 7.6(1H, s, =CH) |
| 133 | 2.7 & 3.15(2H, 2dd, non equivalent ArCH$_2$), 3.7 (3H, s, OCH$_3$), 3.84(3H, s, CO$_2$CH$_3$), 4.1(1H, m, Het-CH), 4.22(2H, s, SCH$_2$Ar), 4.3(1H, m, Het-CH), 4.44 (1H, m, Het-CH), 7.14–7.55(9H, m, ArH), 7.6(1H, s, =CH) |
| 134 | 3.72(3H, s, OCH$_3$), 3.84(3H, s, CO$_2$CH$_3$), 4.34 (1H, m, Het-CH), 4.38(2H, s, SCH$_2$Ar), 4.55(1H, m, Het-CH), 5.00(1H, m, Het-CH), 7.15–7.5(7H, m, ArH), 7.6 (1H, s, =CH) |
| 135 | 3.7(3H, s, OCH$_3$), 3.78(1H, m, Het-CH), 3.86 (3H, s, CO$_2$CH$_3$), 4.25(2H, s, SCH$_2$Ar), 4.32(1H, m, Het-CH), 5.5(1H, m, Het-CH), 7.1–7.52(7H, m, ArH), 7.6 (1H, s, =CH) |
| 136 | 1.03(3H, br s, CH$_2$CH$_3$), 1.75(2H, br s, CH$_2$CH$_3$), 3.7 (3H, s, OCH$_3$), 3.84(3H, s, CO$_2$CH$_3$), 3.95(1H, m, Het-CH), 4.28(2H, s, SCH$_2$Ar), 5.1(1H, m, Het-CH), 7.14–7.54 (9H, m, ArH), 7.6(1H, s, =CH) |
| 137 | 3.45(3H, s, CH$_2$OCH$_3$), 3.54(2H, m, CH$_2$OCH$_3$), 3.72 (3H, s, OCH$_3$), 3.84(3H, s, CO$_2$CH$_3$), 4.2(1H, m, Het-CH), 4.28(2H, s, SCH$_2$Ar), 5.4(1H, d, Het-CH), 7.15–7.54 (9H, m, ArH), 7.6(1H, s, =CH) |
| 138 | 2.66(3H, s, CH$_3$S), 3.73(3H, s, OCH$_3$), 3.89 (3H, s, CO$_2$CH$_3$), 4.43(2H, s, CH$_2$S), 7.1–7.53 (6H, m, ArH), 7.62(1H, s, =CH), 7.97(1H, d, ArH), 8.07 (1H, s, ArH) |
| 139 | 3.12(2H, m, PhSCH$_2$), 3.71(3H, s, OCH$_3$), 3.87 (3H, s, CO$_2$CH$_3$), 4.03(1H, m, Het-CH), 4.15(2H, m, Het-CH),(4.38(2H, m, SCH$_2$), 7.14(1H, m, ArH), 7.2–7.55 (8H, m, ArH), 7.60(1H, s, =CH), |

Test Example A

Compounds are assessed for activity against one or more of the following:

a) Foliar tests

*Phytophthora infestans*: late tomato blight (PI)
*Plasmopara viticola*: vine downy mildew (Pv)
*Erysiphe graminis*: barley powdery mildew (EG)
*Pyricularia cryzae*: rice blast (PO)
*Pellicularia sasakii*: rice sheath blight (PS)
*Botrytis cinerea*: grey mould of tomato (BC)
*Venturia inaequalis*: apple scab (VI)

Aqueous solutions or dispersions of the compounds at the desired concentration, including a wetting agent, were applied by spray or by drenching the stem base of the test plants. These plants were then inoculated with appropriate test pathogens and kept under controlled environment conditions suitable for maintaining plant growth and development of the disease. After an appropriate time, the degree of infection of the leaf surface was visually estimated. Compounds were considered active if they gave greater than 50% control of the disease at a concentration of 125 ppm (w/v) or less.

b) Soil pathogen test

In this tests compounds were assessed for activity against *Rhizoctonia solani* (RS)

Flasks containing maize meal/sand were inoculated with the test fungus and then incubated. The maize meal/sand cultures were used to infest potting compost which was then put into plastic pots. Aqueous solutions or dispersions of the compounds, including a wetting agent, were added to the pots to give a desired concentration of compound in each pot. Control pots were set up by adding similar solutions or dispersions without the test compound. Immediately after application of the test compound each pot was sown with a number of cabbage seeds, The seeds were covered with treated infested soil and the pots incubated under controlled environment conditions suitable for plant growth and development of the disease, The number of emerged cabbage seedlings is counted and percentage disease control calculated by comparison with the untreated infested pots.

Compounds were considered active if they gave greater than 50% control of the disease at a concentration of 100 parts by weight of compound or less per million parts by volume of soil.

Activities were demonstrated as follows (+ = active).

| Compound No | PI | PV | EG | PO | PS | BC | VI | RS |
|---|---|---|---|---|---|---|---|---|
| 1 | + | + | + | + | + |   | + |   |
| 2 | + | + | + | + | + |   | + | + |
| 4 | + | + |   | + |   |   | + |   |
| 5 |   |   |   | + | + |   | + |   |
| 6 | + | + |   |   |   |   | + |   |
| 7 |   |   |   | + | + |   | + |   |
| 8 |   | + |   |   |   |   | + |   |
| 10 | + | + | + | + | + |   |   |   |
| 11 | + | + | + |   | + |   | + |   |
| 12 | + | + | + | + | + |   | + |   |
| 13 | + | + | + | + | + |   | + |   |
| 14 | + | + | + |   | + |   | + |   |
| 15 | + | + | + | + |   |   | + |   |
| 16 | + | + | + | + | + | + | + |   |
| 17 | + | + |   | + |   |   | + |   |
| 19 |   |   |   |   |   |   | + |   |
| 20 | + | + | + | + | + |   | + |   |
| 21 | + | + |   | + | + |   | + |   |
| 22 | + | + |   | + |   | + | + |   |
| 23 | + | + |   | + | + |   | + |   |
| 24 | + | + | + | + | + |   | + |   |
| 25 | + | + | + | + | + |   | + |   |
| 26 | + | + |   | + | + |   |   |   |
| 27 | + | + |   | + |   |   | + | + |
| 28 | + | + |   | + | + |   | + |   |
| 29 | + | + | + |   | + |   | + |   |
| 30 | + | + |   | + | + |   | + |   |
| 31 |   | + |   |   |   |   | + |   |
| 32 | + | + |   | + | + |   | + |   |
| 33 | + | + |   | + | + |   | + |   |
| 34 |   |   |   | + |   |   |   |   |
| 35 | + | + |   | + |   |   |   |   |
| 36 |   | + | + | + |   |   |   |   |
| 37 |   | + | + |   |   |   | + |   |
| 38 | + | + | + | + | + |   | + |   |
| 39 |   | + | + |   |   |   | + |   |
| 40 |   | + |   |   |   |   | + |   |
| 41 | + | + |   | + |   |   | + |   |
| 42 | + | + | + |   | + |   |   |   |
| 43 | + | + |   | + |   |   | + |   |
| 44 | + | + | + |   |   |   | + |   |
| 45 |   | + | + |   | + |   | + |   |
| 46 |   |   |   |   | + |   | + |   |
| 47 | + | + | + | + | + | + | + | + |
| 48 | + | + |   | + |   |   | + |   |
| 49 | + | + | + | + | + | + | + | + |
| 50 |   | + | + | + | + |   | + |   |
| 51 | + | + | + | + | + |   | + |   |
| 52 | + |   |   | + | + |   | + |   |
| 53 |   | + | + |   | + |   | + |   |
| 54 | + | + |   | + |   |   | + |   |

19
-continued

Activities were demonstrated as follows (+ = active).

| Compound No | PI | PV | EG | PO | PS | BC | VI | RS |
|---|---|---|---|---|---|---|---|---|
| 55 |   | + |   | + |   |   | + |   |
| 56 |   |   |   |   |   | + | + |   |
| 57 |   | + |   |   | + |   | + |   |
| 58 |   |   |   |   |   |   | + |   |
| 59 | + | + | + |   |   |   | + |   |
| 60 | + | + | + | + |   |   | + |   |
| 61 | + | + | + | + | + |   | + | + |
| 62 | + | + | + | + | + | + | + | + |
| 63 |   |   |   |   |   |   | + |   |
| 64 | + | + | + | + | + |   | + |   |
| 65 |   | + | + | + |   |   | + |   |
| 66 |   | + |   | + | + |   | + |   |
| 67 |   | + | + | + | + |   | + |   |
| 68 | + | + | + |   | + | + | + |   |
| 69 |   | + |   |   |   |   | + |   |
| 70 |   | + |   |   |   |   |   |   |
| 71 | + | + |   |   |   |   | + |   |
| 72 |   | + |   |   |   |   | + |   |
| 73 | + |   |   |   | + |   | + |   |
| 74 |   | + |   |   |   |   | + |   |
| 75 |   |   | + | + |   |   | + |   |
| 76 |   |   |   | + |   |   | + |   |
| 77 | + |   |   | + |   | + | + |   |
| 78 | + | + | + | + | + |   | + |   |
| 79 | + | + | + | + |   |   | + |   |
| 80 | + | + |   | + |   |   | + |   |
| 81 | + | + | + | + | + | + | + | + |
| 82 | + | + |   | + |   |   | + |   |
| 83 | + | + | + | + |   |   | + | + |
| 84 | + | + |   |   |   |   |   |   |
| 85 |   | + | + |   | + |   | + |   |
| 87 | + | + | + | + | + | + | + |   |
| 88 |   | + |   | + |   |   | + |   |
| 89 |   | + | + |   | + |   | + |   |
| 90 |   | + | + | + | + |   | + |   |
| 91 |   | + |   | + |   |   | + |   |
| 92 |   |   |   |   |   |   | + |   |
| 93 | + |   |   |   |   |   | + |   |

Test Example B

This example illustrates the insecticidal activity of compounds of the invention.

1 ml Aliquots of an acetone solution containing test compound at various concentrations were applied to cotton wool dental rolls 1 cm×2 cm, contained in glass vials 2 cm diameter×5 cm long. After drying, the treated materials were then impregnated with 1 ml of nutrient solution, infested with first instar larvae of sheep blow fly (*Lucilia sericata*), closed by a cotton wool plug and held at 25° C. for 24 hours. For the controls the mortality was <5% whereas the compounds of Examples 1, 4, 6, 10, 12, 13, 20, 24–26, 30–32, 38–41, 46, 49, 51, 53, 56, 60, 61, 64, 81 and 90 had an $LC_{50}$ of less than 300 ppm.

We claim:

1. A compound of formula I

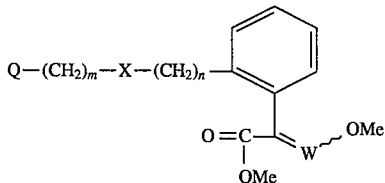

(I)

wherein

X is oxygen or sulphur,

W is CH or N, m is 0 or 1, and n is 0 or 1 and

Q is

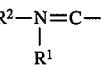

where $R^1$ is alkyl, alkoxy or alkylthio, and $R^2$ is thienyl; furyl; pyrrolyl; pyridyl; pyrimidinyl; pyrazolyl; thiazolyl; oxazolyl; benzimidazolyl; tetrazolyl; benzoxazolyl; thiadiazolyl; triazolyl; imidazolyl; benzothiazolyl; pyrrolidinyl; morpholinyl; thiomorpholinyl; fully or partially hydrogenated thienyl, furanyl, pyrrolyl, thiazolyl, oxazolyl, oxazinyl, thiazinyl, pyridinyl and azepinyl; optionally substituted cyloalkyl or optionally substituted alkyl containing at least 5 carbon atoms; phenyl substituted by one or more groups selected from halogen, optionally substituted alkyl, alkoxy, haloalkoxy, aryloxy, alkylthio and alkoxycarbonyl; and when $R^1$ is alkyl or alkoxy, or, when W is nitrogen, $R^2$ can also be unsubstituted phenyl, the optional substituents being halogen, alkoxy, alkylthio, alkylcarbonyl and phenyl in which the phenyl is itself optionally substituted by halogen, hydroxy, alkoxy, alkyl, trifluoronothyl and nitro, and acid addition salts of compounds which are basic and basic addition salts of any compounds which are acidic.

2. A compound according to claim 1 in which $R^1$ is methylthio or methyl.

3. A compound according to claim 1 in which n is 1, m is 0 and X is S.

4. A compound according to claim 1 in which W is CH.

5. A compound according to claim 1 in which W is N.

6. A method of combatting fungi at a locus infested or liable to be infested therewith, which comprises apply to the locust a compound claimed in claim 1.

7. A method of combatting fungi at a locus infested or liable to be infested therewith, which comprises apply to the locust a compound claimed in claim 2.

8. A method of combatting fungi at a locus infested or liable to be infested therewith, which comprises apply to the locust a compound claimed in claim 3.

9. A method of combatting fungi at a locus infested or liable to be infested therewith, which comprises apply to the locust a compound claimed in claim 4.

10. A method of combatting fungi at a locus infested or liable to be infested therewith, which comprises apply to the locust a compound claimed in claim 5.

11. A fungicidal composition comprising a compound as claimed in claim 1 in admixture with a fungicidably acceptable diluant or carrier.

12. A fungicidal composition comprising a compound as claimed in claim 2 in admixture with a fungicidably acceptable diluant or carrier.

13. A fungicidal composition comprising a compound as claimed in claim 3 in admixture with a fungicidably acceptable diluant or carrier.

14. A fungicidal composition comprising a compound as claimed in claim 4 in admixture with a fungicidably acceptable diluant or carrier.

15. A fungicidal composition comprising a compound as claimed in claim 5 in admixture with a fungicidably acceptable diluant or carrier.

* * * * *